United States Patent
Arramon et al.

(10) Patent No.: US 11,648,058 B2
(45) Date of Patent: May 16, 2023

(54) ROBOTIC SYSTEM AND METHOD FOR BONE PREPARATION FOR INTERVERTEBRAL DISC PROSTHESIS IMPLANTATION

(71) Applicant: Simplify Medical Pty Ltd, Paddington (AU)

(72) Inventors: Yves Arramon, Sunnyvale, CA (US); David Hovda, Mountain View, CA (US); Michael Sherman, Memphis, TN (US)

(73) Assignee: Simplify Medical Pty Ltd, Melbourne (AU)

( * ) Notice: Subject to any disclaimer, the term of this patent is extended or adjusted under 35 U.S.C. 154(b) by 700 days.

(21) Appl. No.: 16/578,919

(22) Filed: Sep. 23, 2019

(65) Prior Publication Data

US 2020/0093542 A1    Mar. 26, 2020

Related U.S. Application Data

(60) Provisional application No. 62/735,666, filed on Sep. 24, 2018.

(51) Int. Cl.
*A61B 34/10*    (2016.01)
*A61B 34/00*    (2016.01)
(Continued)

(52) U.S. Cl.
CPC ............. *A61B 34/10* (2016.02); *A61B 34/20* (2016.02); *A61B 34/30* (2016.02); *A61B 34/74* (2016.02);
(Continued)

(58) Field of Classification Search
CPC . A61F 2/44; A61F 2/442; A61F 2/447; A61B 34/76; A61B 34/30; A61B 34/20; A61B 34/00; A61B 34/10
See application file for complete search history.

(56) References Cited

U.S. PATENT DOCUMENTS

| | | | |
|---|---|---|---|
| 6,226,548 B1 | 5/2001 | Foley et al. | |
| 6,340,363 B1 | 1/2002 | Bolger et al. | |

(Continued)

FOREIGN PATENT DOCUMENTS

| | | |
|---|---|---|
| EP | 2381858 B1 | 11/2018 |
| JP | 2017536909 A | 12/2017 |

(Continued)

OTHER PUBLICATIONS

International Search Report and Written Opinion for PCT/AU2019/000114 dated Jan. 16, 2020.

*Primary Examiner* — Christopher J Beccia
(74) *Attorney, Agent, or Firm* — Hoffman Warnick LLC

(57) ABSTRACT

Systems and methods for robotically preparing a disc space are provided for implantation of an intervertebral prosthetic disc. The system includes three-dimensional modeling to identify positions of vertebrae adjacent a surgical site and a disc selection interface in a computing system to allow the surgeon to select an intervertebral disc prosthesis for implantation. A bone cutting interface allows the surgeon to determine a bone cutting pattern tailored to both the three-dimensional positions of the vertebrae and the selected intervertebral disc. A robot controls a cutting device or guides a cutting device to cut the vertebral bone in the bone cutting pattern.

15 Claims, 5 Drawing Sheets

(51) Int. Cl.
*A61B 34/20* (2016.01)
*A61B 34/30* (2016.01)
*A61F 2/44* (2006.01)
*A61B 17/02* (2006.01)

(52) U.S. Cl.
CPC .............. *A61B 34/76* (2016.02); *A61F 2/442* (2013.01); *A61B 2017/0256* (2013.01); *A61B 2034/102* (2016.02); *A61B 2034/105* (2016.02); *A61B 2034/107* (2016.02); *A61B 2034/108* (2016.02); *A61B 2034/2057* (2016.02); *A61B 2034/2074* (2016.02); *A61F 2/4455* (2013.01)

(56) References Cited

U.S. PATENT DOCUMENTS

| | | |
|---|---|---|
| 7,542,791 B2 | 6/2009 | Mire et al. |
| 7,567,834 B2 | 7/2009 | Clayton et al. |
| 7,575,599 B2 | 8/2009 | Villiers et al. |
| 7,585,326 B2 | 9/2009 | De Villiers et al. |
| 7,637,913 B2 | 12/2009 | De Villiers et al. |
| 7,753,956 B2 | 7/2010 | De Villiers et al. |
| 8,043,295 B2 | 10/2011 | Reed et al. |
| 8,100,979 B2 | 1/2012 | Felt et al. |
| 8,206,449 B2 | 6/2012 | Jansen et al. |
| 8,337,508 B2 | 12/2012 | Lavallee et al. |
| 8,394,144 B2 | 3/2013 | Zehavi et al. |
| 8,685,035 B2 | 4/2014 | De Villiers et al. |
| 8,764,833 B2 | 7/2014 | De Villiers et al. |
| 8,840,629 B2 | 9/2014 | Bonutti |
| 8,897,514 B2 | 11/2014 | Feikas et al. |
| 8,992,580 B2 | 3/2015 | Bar et al. |
| 9,011,544 B2 | 4/2015 | Arramon et al. |
| 9,125,680 B2 | 9/2015 | Kostrzewski et al. |
| 9,351,846 B2 | 5/2016 | De Villiers et al. |
| 9,545,233 B2 | 1/2017 | Sirpad et al. |
| 9,782,229 B2 | 10/2017 | Crawford et al. |
| 10,034,711 B2 | 7/2018 | Greenwald et al. |
| 2006/0084986 A1 | 4/2006 | Grinberg et al. |
| 2007/0198022 A1 | 8/2007 | Lang et al. |
| 2008/0195081 A1 | 8/2008 | Moll |
| 2009/0234217 A1 | 9/2009 | Mire et al. |
| 2009/0299477 A1 | 12/2009 | Clayton et al. |
| 2011/0306873 A1 | 12/2011 | Shenai et al. |
| 2014/0378999 A1 | 12/2014 | Crawford et al. |
| 2015/0032164 A1 | 1/2015 | Crawford et al. |
| 2015/0182288 A1* | 7/2015 | Greenwald ............ A61B 34/20 606/279 |
| 2015/0366624 A1 | 12/2015 | Kostrzewski et al. |
| 2017/0265774 A1 | 9/2017 | Johnson et al. |
| 2018/0110573 A1 | 4/2018 | Kostrzewski |
| 2018/0125598 A1 | 5/2018 | McAfee |
| 2018/0168757 A1* | 6/2018 | Bono ..................... A61B 34/30 |
| 2018/0199951 A1 | 7/2018 | Chappuis et al. |
| 2018/0221008 A1 | 8/2018 | Todorov et al. |
| 2018/0221097 A1 | 8/2018 | Bonutti |

FOREIGN PATENT DOCUMENTS

| | | |
|---|---|---|
| WO | WO-2010064234 A2 | 6/2010 |
| WO | WO-2016131903 A1 | 8/2016 |
| WO | WO-2016154356 A1 | 9/2016 |
| WO | WO-2018167246 A1 | 9/2018 |
| WO | WO-2020061609 A1 | 4/2020 |

* cited by examiner

ROBOTIC SYSTEM AND METHOD FOR BONE PREPARATION FOR INTERVERTEBRAL DISC PROSTHESIS IMPLANTATION

CROSS-REFERENCE TO RELATED APPLICATIONS

This application claims the benefit of U.S. Provisional No. 62/735,666, filed Sep. 24, 2018, the entire content of which is incorporated herein by reference.

BACKGROUND OF THE INVENTION

1. Field of the Invention

The present invention relates to medical devices and methods. More specifically, the invention relates to intervertebral prosthetic discs and systems and methods for robotically preparing a disc space for implantation of an intervertebral prosthetic disc.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs. With age, intervertebral disks begin to shrink. In some cases, they may collapse completely and cause the bones to rub against one another. This is also referred to as osteoarthritis.

When a damaged intervertebral disc causes a patient pain and discomfort, surgery is often required. Typically, surgical procedures for treating damaged intervertebral discs involve discectomy (partial or total removal of a disc), often followed by interbody fusion of the superior and inferior vertebrae adjacent to the disc or implantation of an intervertebral prosthetic disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together. Spinal fusion eliminates motion between the vertebrae. Fusion is an option when motion is the source of pain.

An alternative to spinal fusion which doesn't limit patient mobility is intervertebral disc replacement (TDR), also called total disc arthroplasty. The TDR procedure involves removing the natural disk from between the vertebrae and replacing it with and artificial disc prosthesis. Several types of intervertebral disc prosthesis are currently available. For example, one type of intervertebral disc prosthesis includes upper and lower prosthesis plates which locate against and engage the adjacent vertebral bodies and a mobile core positioned between the plates. The core has upper and lower convexly curved surfaces and the plates have corresponding, concavely curved recesses which cooperate with the curved surfaces of the core. This allows the plates to slide over the core to allow spinal movement to take place.

In one alternative arrangement, the core is eliminated and the upper and lower prosthesis plates of the intervertebral disc prosthesis articulate about one another in a ball and socket articulation arrangement. Typical drawbacks of the known intervertebral disc prosthesis include insufficient resistance to wear and tear, restricted range of motion, undesirable contact between plates causing potential wear, excessive disc height not appropriately matched to patient anatomy and/or insufficient ability of the prosthesis to adhere to vertebral bone. These drawbacks have been acknowledged and new intervertebral disc prosthesis are being developed which have improved properties. However, positioning the intervertebral disc prosthesis accurately for optimal performance continues to be problematic.

Therefore, a need exists for improved intervertebral disc prosthesis implantation techniques. Ideally, such improved techniques would reduce or eliminate improperly placed prostheses and improved performance and pain relief for patients. At least some of these objectives will be met by the inventions described herein.

2. Description of the Background Art

A variety of intervertebral disc prosthesis designs and methods of implanting are described in described in U.S. Pat. Nos. 7,442,211; 7,531,001; 7,575,599; 7,585,326; 7,637,913; 7,753,956; 8,206,449; 8,685,035; 8,764,833; 9,011,544 and 9,351,846, each of which is incorporated herein by reference in its entirety.

BRIEF SUMMARY OF THE INVENTION

According to one aspect of the invention, a surgical method for preparing a vertebral disc space for implantation of an intervertebral disc prosthesis comprises identifying positions of first and second vertebrae and generating and storing position data for the positions of the first and second vertebrae in a computing system; selecting an intervertebral disc prosthesis to be implanted between the first and second vertebrae; determining a desired location for the selected intervertebral disc prosthesis with respect to the positions of the first and second vertebrae and storing position data for the intervertebral disc prosthesis location; determining a preselected pattern of bone to be cut based on the position data for the first and second vertebrae and the position data for the selected intervertebral disc prosthesis; and robotically guiding a cutting device to cut the bone in the preselected pattern to fit the selected intervertebral disc prosthesis.

According to another aspect of the invention, a system for implanting an intervertebral disc prosthesis in a vertebral disc space comprises a 3D modeling system for creating a 3D model of first and second vertebra adjacent the disc space and identifying positions of the first and second vertebrae and generating and storing position data for the positions of the first and second vertebrae; a computing system for storing and processing the 3D model and the position data; a disc selection interface on the computing system configured to allow the surgeon to select an intervertebral disc prosthesis to be implanted from a plurality of available intervertebral disc prosthesis based on the 3D model and position data for the first and second vertebrae; a bone cutting interface on the computing system configured to determine a bone cutting pattern based on the position data for the first and second vertebrae and the selected intervertebral disc prosthesis; a cutting device for cutting vertebral bone; and a robot configured to guide the cutting device to cut the bone in the bone cutting pattern to fit the selected intervertebral disc prosthesis.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
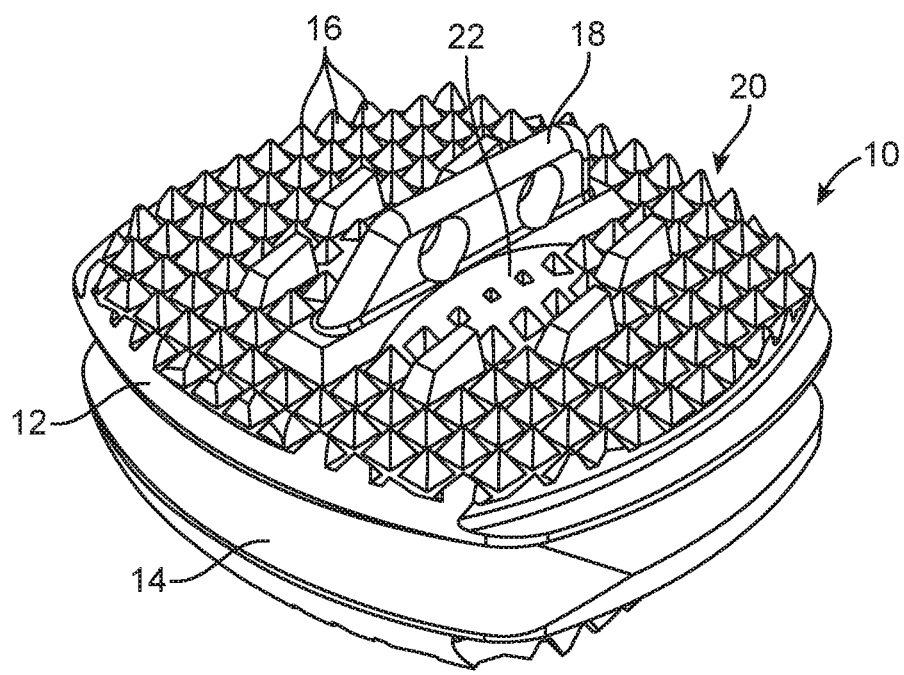
FIG. 1 is a perspective view of an intervertebral disc prosthesis with a central fin.

Positioning of an intervertebral disc prosthesis properly in the spine is an important part of a successfully total disc arthroplasty (TDR) procedure. The position of the implant in the intervertebral space can influence the range of motion, implant behavior and clinical result. Potential improper positions include discs not placed on the midline of the adjacent vertebrae, discs not placed in the proper position in the anterior posterior direction, discs rotated within the disc space and discs in which the upper and lower disc components are not aligned with one another or with the endplates of the superior or inferior vertebral bodies. Surgeon experience, surgeon training, use of imaging modalities and patient anatomy are all factors which can influence accuracy of disc placement.

In traditional disc arthroplasty procedures, the vertebrae adjacent to the intended location of the intervertebral disc prosthesis are prepared for prosthetic disc implantation by using osteotomes, drills, burrs, cutters or other instruments to prepare the vertebral surface for receiving the intervertebral disc prosthesis. The preparation of the vertebral surfaces differs depending on the type of intervertebral disc prosthesis selected to be implanted. The surgeon may need to reshape (or shape) the surfaces of the vertebrae to receive a flat or shaped endplate or to cut a channel to receive a fin or teeth of an endplate. When these preparation procedures are done manually there is reasonable opportunity for error or inaccuracies that will translate directly to an improper placement of the final intervertebral disc prosthesis and potentially a suboptimal clinical outcome. An experienced surgeon learns to shape the vertebra endplate surfaces to match the intervertebral disc prosthesis, however, even an experienced surgeon can require several iterations of removing bone and retrying a sizer or trial implant before getting the proper surface shape. This trial and error shaping of the bone extends the surgery time and requires repeated X-ray exposure as each time the surgeon fits the trial implant they check the fit on X-ray or fluoroscopy. Patient anatomy can vary and cause further difficulty in correctly shaping the vertebral surfaces to match an intervertebral disc prosthesis.

In one example of improper positioning in the anterior posterior direction, cases have been reported of prosthesis dislocation caused by the implantation process, during which the intervertebral disc prosthesis was implanted too anteriorly. Two cases of intervertebral disc prosthesis dislocation within 3 months of surgery were reportedly caused by the disc being implanted too anteriorly and the presence of shear forces caused by this anterior position. Aunoble, S., P. Donkersloot, and J. C. Le Huec. "Dislocations with Intervertebral Disc Prosthesis: Two Case Reports." *European Spine Journal* 13.5 (2004): 464-467. *PMC*. Web. 27 Aug. 2018. In these cases, the patients required revision to a fusion procedure.

Positioning of the intervertebral disc prosthesis center of rotation at a natural center of rotation for the segment of the spine can also be important with certain intervertebral disc prostheses. Discs of the ball and socket type described above are particularly sensitive to requiring placement with the disc center of rotation at or very close to the spinal segment center of rotation. Since the anatomical center of rotation cannot be determined based on visible landmarks, automated systems for determining natural anatomical center of rotation and locating the intervertebral disc prosthesis center of rotation at the natural anatomical center of rotation would be useful. Placement of the intervertebral disc prosthesis center of rotation in a non-natural anatomical position can create improper motion and lead to other unintended problems for the patient such as increased forces on adjacent tissues and adjacent vertebral discs.

Robotic and automated systems and methods for preparing vertebrae for an intervertebral disc implant as described herein can significantly improve accuracy of intervertebral disc prosthesis positioning and thereby reduce the pain and discomfort a patient may experience due to improper disc placement. These automatic vertebrae preparation systems can also give surgeons confidence in the accuracy of disc positioning, decrease surgery and anesthesia time and reduce blood loss. The automated systems for preparation of vertebrae can also standardize prosthesis placement between surgeons leading to more uniform results.

Referring to FIG. 1, one example of an intervertebral disc prosthesis 10 for insertion between adjacent vertebrae includes an upper plate 12, a lower plate 14 and a core (not shown) between the upper and lower plates. The core is retained between the upper and lower plates by a retention feature and is designed to allow the plates to slide over the upper and lower surfaces of the core in the anterior/posterior direction and in the lateral direction and to allow the plates to articulate and rotate with respect to each other and the core.

The upper plate 12 includes an outer surface 20 having a plurality of serrations 16, pyramid shapes or truncated pyramid shapes. A fin 18 extends from a center of the outer surface 20 in an anterior/posterior direction. However, the fin 18 can also be positioned in other orientations for lateral or posterior/lateral insertion techniques. The outer surface 20 also includes a domed shaped central portion 22 to accommodate the natural anatomical concavity in the lower surfaces of the vertebrae. The core cannot be seen between the plates, however further details of an example of a core can be found in U.S. Pat. No. 8,764,833 which is incorporated herein by reference in its entirety.

The lower plate 14 has an outer surface which may have the same shape as the outer surface of the upper plate with a fin, dome and serrations. However, in other embodiments the upper and lower plates can have different configurations to more closely match the anatomy of the patient. For example, the upper or superior plate 12 may have a somewhat domed shaped central portion 22 to accommodate the natural anatomical concavity in the lower surfaces of the vertebra above the disc while the lower plate 14 may have a smaller dome or no dome to more closely match the anatomy of the upper surfaces of the vertebra below the natural disc to be replaced. The upper and lower plates 12, 14 can both have one central fin 18 or more than one fin. In one example, the upper plate 12 has a single central fin 18 designed to be placed on the midline of the vertebrae while the lower plate 14 has two symmetrically place fins designed to be placed symmetrically about the midline. In addition, one or both of the upper and lower plates can be provided with non-parallel upper and lower surfaces to accommodate spinal lordosis.

The robotic systems and methods for preparing a vertebral disc space for implantation of an intervertebral disc prosthesis described below can be used to both cut a slot in the vertebrae for receiving the fin 18 shown in FIG. 1 and can be used to shape the surface of the vertebrae to the shape of the disc endplate so that the endplate will locate in a desired location with respect to the adjacent vertebrae. For example, the robotic system can be used to form a concavity, such as a dome shaped concavity, in a specific location or a central location in the upper vertebrae so that the prosthetic disc will fit easily into a predetermined desired location.

Figure 2:
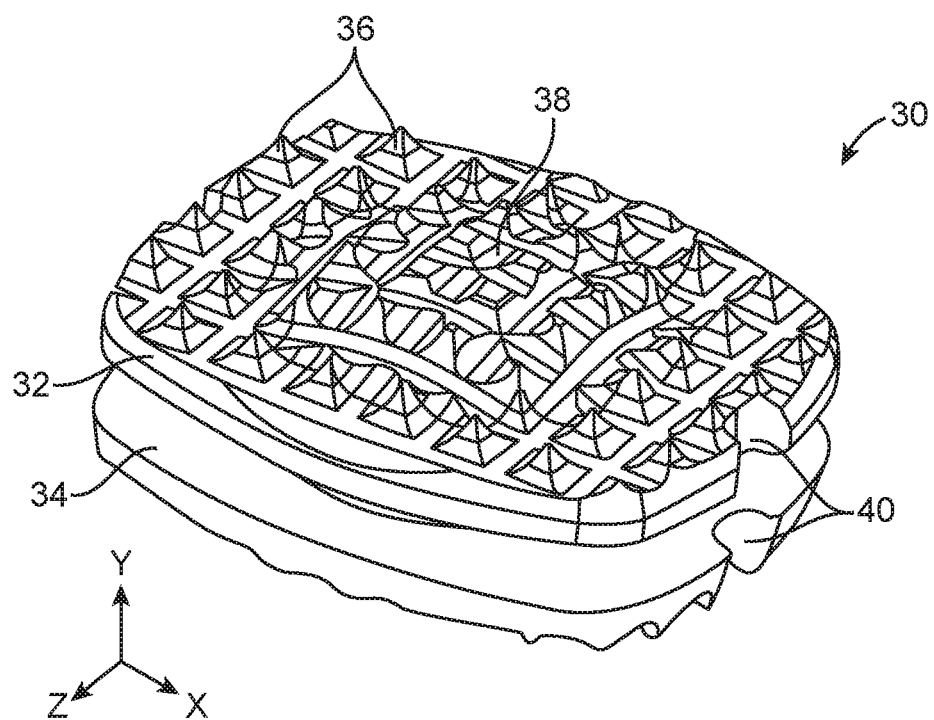
FIG. 2 is a perspective view of an intervertebral disc prosthesis with a central dome.

As shown in FIG. 2, another example of an intervertebral disc prosthesis 30 includes an upper plate 32, a lower plate 34 and a core (not shown) between the upper and lower plates. The upper plate 32 includes an outer surface with a plurality of pyramid shaped and truncated pyramid shaped projections 36 or serrations. The upper plate 32 also has a central domed portion 38 to accommodate the natural anatomical concavity in the lower surfaces of the vertebra. The lower plate 34 has an outer surface which may have the same shape and features as the outer surface of the upper plate a dome and serrations or may have a different shape and features.

As seen in FIG. 2, each of the plates 32, 34 can have a pair of side notches 40 configured for grasping the plate with an insertion instrument. As shown in FIG. 2, the side notches 40 are located centrally between the anterior and posterior of the plates for grasping the plates and insertion from the anterior side of the spine. The insertion instrument (not shown) includes opposing jaws which fit into the two side notches 40. In one preferred embodiment, a single pair of opposition jaws of an insertion instrument is able to grasp both the upper and lower plates 32, 34 by engaging the upper and lower plates both with the same opposing right and left jaws. Once the upper and lower plates 32, 34 are assembled with the core there between and grasped by the insertion instrument, the upper and lower plates and core are held in a fixed configuration and not able to articulate until released from the jaws of the insertion instrument. In the constrained insertion configuration, the upper and lower plates 32, 34 can be parallel, as shown in FIG. 2, or slightly angled with the posterior edges of the plates closer to one another for insertion in a wedge shape from an anterior of the spine. For other insertion directions, such as lateral or posterior, the notches 40 are positioned to allow for the particular insertion direction.

The intervertebral disc prosthesis of FIGS. 1 and 2 are shown as examples of the types of discs shapes that are used for TDR procedures and for which the robotic systems described herein can prepare the vertebral surfaces. Other intervertebral discs may have flanges, screws or other features which can be accommodated by corresponding robotic shaping of the vertebrae.

Figure 3:
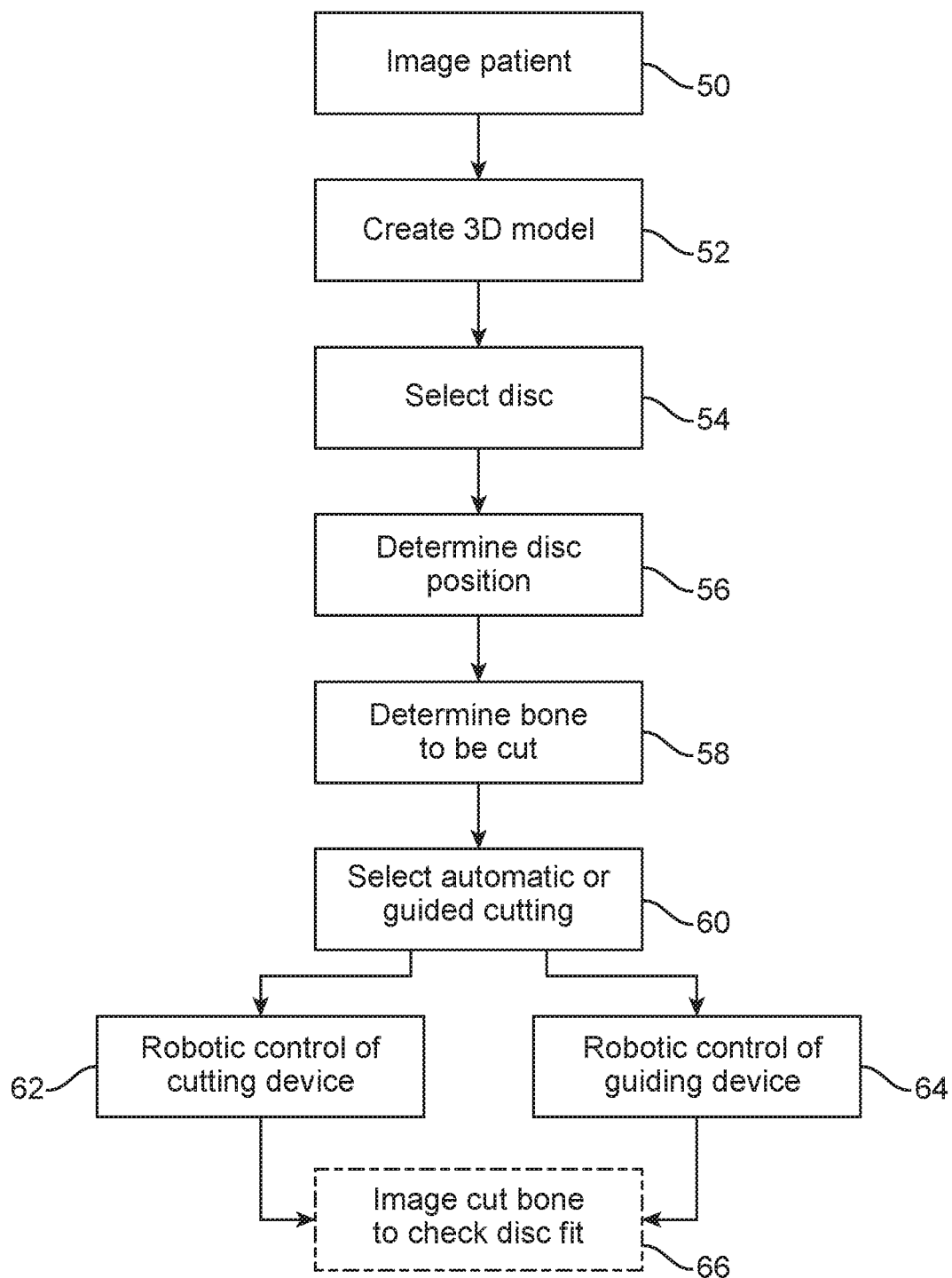
FIG. 3 is a block diagram of a surgical method for robotically preparing a vertebral disc space for implantation of an intervertebral disc prosthesis.

FIG. 3 is a block diagram of a surgical method for robotically preparing a vertebral disc space for implantation of an intervertebral disc prosthesis. As shown in FIG. 3, the surgical method for preparing a vertebral disc space for implantation of an intervertebral disc prosthesis includes a first step 50 of imaging the patient. The step of imaging will be described in further detail below and may include imaging with X-ray, CT scan, MRI, photographs or a combination of these methods. In a second step 52, computer software is then used to create a 3D model of the first and second vertebrae adjacent the location where the intervertebral disc prosthesis is to be placed and data identifying positions of first and second (superior and inferior) vertebrae is generated. Position data for the positions of the first and second vertebrae are stored in a computing system.

In a disc selection step 54, an intervertebral disc prosthesis to be implanted between the first and second vertebrae is selected. The disc may be selected automatically by the computing system based on the 3D model and position data generated in step 52. In the case of automatic implant selection, measurements of the 3D model are made by the computer processor and the processor determines the best fitting intervertebral disc prosthesis based on the 3D model measurements. The best fit is determined for a height, footprint size and/or lordosis for the intervertebral disc prosthesis to be implanted based on the acquired 3D model data. One example of a method for imaging the anatomy of the spine and automatically selecting a spinal implant based on the imaging data is describe in U.S. Pat. No. 7,542,791. Alternatively, the intervertebral disc prosthesis may be selected manually in the selection step 54 by the surgeon based on visual, tactile, radiographic and/or other feedback using trial intervertebral disc prostheses in the size and shape of the available prostheses. However, since the cutting and shaping of the bone has not been performed at this stage in the procedure, manual implant selection may be difficult depending on the anatomy.

In a next step 56 of determining a desired location for the selected intervertebral disc prosthesis, a desired location for the intervertebral disc prosthesis is determined either automatically or manually with respect to the positions of the first and second vertebrae. The position of the desired location is stored as desired disc prosthesis position data. In general, the desired position for the disc prosthesis is located centrally between left and right side edges of the vertebrae on the midline of the spine and with a center of rotation of the disc prosthesis at the natural center of rotation for a healthy disc or the actual center of rotation for a particular patient.

Determination of the natural center of rotation of a healthy disc can be based on studies of quantitative motion analysis which have determined the idealized centers of rotation for each level of the spine in both the sagittal and coronal planes. Alternatively, the determination of the natural centers of rotation can be calculated from measurements of the actual patient in the 3D model either pre-operatively or intraoperatively. The center of rotation is measured in the sagittal plane between the extremes of motion using maximum flexion and extension X-ray images or in the 3D model. In the cervical spine, the center of rotation is generally in the posterior portion of the disc and in the vertebral body below the disc space. In the lumbar spine, the center of rotation is generally just posterior of the anterior/posterior center of the disc space and just at the top of the lower vertebral body. Methods for calculating the center of rotation are described in John A. Hipp & Nicholas D. Wharton, Quantitative Motion Analysis (QMA) of Motion-Preserving and Fusion Technologies for the Spine, Motion Preservation Surgery of the Spine: *Advanced Techniques and Controversies*: Expert Consult: Online and Print, 1e, Jun. 12, 2008, p. 85-97, Elsevier Inc. Additionally, spine diagnostic imaging systems which can preoperatively determine centers of rotation are available, such as from Ortho Kinematics, Inc.

Traditional cervical intervertebral disc replacements which incorporate a ball-and-socket design (e.g. ProDisc-C, Discover), but no translation features, provide a fixed center of rotation and thus require a precise device placement to replicate anatomic centers of rotation and restoration of natural kinematics. With ball-and-socket devices, posterior placement of the device is essential to ensure the center of rotation of the device overlaps the natural center of rotation for a healthy disc. Anterior placement of a ball-and-socket device can theoretically place increased stress on the facet joints, risk facet arthrosis and accelerated adjacent segment degeneration and even cause expulsion. Intervertebral disc prosthesis replacements with independent translation and rotation with a mobile center of rotation design (Kineflex®|C, Simplify® Disc) have the advantage of providing normal kinematics over a range of device positions.

After the disc position is determined either automatically or manually, the next step 58 is to generate a plan or a model of bone to be cut or shaped. The plan of bone to be shaped is computed based on the 3D model of the spine and position data for the first and second vertebrae determined in step 52, the disc selected in step 54 and the position data for the selected intervertebral disc prosthesis determined in step 56. The computer processor determines the bone to be cut, shaped or bone to not be cut and saves this information as one or more of the following types of information 1) a trajectory for a cutting tool; 2) a desired pattern for motion of a cutting tool; 3) a desired location of a no cut area to prevent cutting at the no cut area; 4) a predetermined plane for cutting; 5) a predetermined depth for cutting; 6) a predetermined depth and radius for shaping to receive a dome; 7) a location and trajectory for access to the disc space from the posterior or lateral side of the disc; 8) a desired pattern of bone removal of the uncinate process; and 9) a location, size and shape of osteophytes to be removed. The amount of bone to be cut or shaped should be optimized to maintain bone strength while minimize chances of disc prosthesis subsidence. The determination of bone to be cut or shaped will be described further below in connection with a number of specific examples.

The 3D model and position data generated in step 52 is preferably used to track the precise location of the two adjacent vertebrae during cutting. Tracking of the vertebrae can be done by various techniques. In a first technique, radio-opaque markers are affixed to the two vertebrae which can be used to identify the precise positions of the vertebrae. In a second technique, anatomical landmarks are used to provide position information to the commuting system. In another technique, passive-reflective or electromagnetic transmitter/detectors can be secured to the two vertebrae to automatically update the computing system to any changes in position of the vertebrae. In a further technique, intraoperative camera images are combined with the 3D model data to map the surface of the vertebrae and the location of the mapped surface is tracked via the computing system by continuous review of contemporaneous camera images of the surgical site. As another option, infrared camera imaging technology can be used for intraoperative tracking the vertebrae in the 3D model.

In a next step 60 before cutting begins, the user (surgeon) can select between automatic (robotic) cutting and robotic guided manual cutting of the bone. In some cases, the system provides only one of these options for various reasons, such as, only one option is applicable to the situation or only one option is approved for use in the circumstances. If the robotic control of the cutting device option 62 is chosen, the robot end effector grasps the appropriate cutting device and manipulates the surgical instrument to robotically cut bone according to the planning information determined in step 58. The cutting device may include a cutter, such as a slot cutter, osteotome, burr, drill, ultrasonic cutter, bone saw or other cutting instrument or surgical instrument. In a method of robotic control of the cutting device the robot is controlled to cut the bone in a desired pattern without a surgeon's hand on the cutting device or tool. Surgeon oversight of the robotic cutting can be provided with the surgeon positioned beside the patient having an off switch or pedal adjacent the surgical site. Alternatively, the surgeon can be positioned at the computer interface and can adjust or stop the cutting from the computer interface.

If the robotic control of a guiding device option 64 is selected, a guiding device is connected to the robot end effector and positioned by the robot with respect to the patient. A cutting device or surgical instrument is positioned in or grasped by the guiding device. In this method, the surgeon controls or manipulates the cutting device while supported by the guiding device such that the location of cutting is robotically controlled by the guiding device and the speed of movement and activation of the cutting device is controlled by the surgeon. In one option, the guiding device allows free movement of the cutting device by the surgeon within an area determined to be cut and prevents movement of the cutting device into locations not designated as areas to be cut (no cut location). In one example, the robotic guiding device acts as both a depth stop to control the depth of cutting and a cutting plane control to allow cutting only in a desired plane. In robotic control of the guiding device, the guiding device guides the cutting device robotically to a desired position for cutting the bone and the surgeon manually actuates the cutting device or tool for cutting the bone. Robotic control of the guiding device may alternatively include robotically guiding the guiding device to prevent cutting bone at a location or region identified as a no cut location.

The robot used in the present invention may be any of the known surgical robots including floor mounted or table mounted robots. Surgical robots generally operate in one of the following approaches: 1) robot guidance; 2) automated robotic operation; or 3) surgeon guided robotic operation. Examples of the robot guidance approach include the Mazor Renaissance robot and the Globus ExcelsiusGPS robot which both allow instruments to be positioned and screws to be placed through a rigid robotic arm that locks into a position and aligns to the patient according to a surgeon's plan. With robot guidance, the robot does not move the instrument or activate the instrument, but provides a guide tube which aligns the instrument to the surgical site. Another example of robotic guidance is the Stryker Mako robot used for knee replacement surgery. The Mako System assists in performing surgery based on a personalized pre-operative plan prepared by the surgeon and then the surgeon guides the robotic-arm within a pre-defined area defined in the pre-operative plan.

Surgeon controlled robotic surgery systems allow the surgeon's hand movements to be translated to movements within the patient's body. An example of one such surgeon controlled system is the da Vinci System by Intuitive Surgical. The da Vinci System includes a surgical robot and a separate console where the surgeon sits and operates the robot's controls while looking at a magnified image of the surgical site on a monitor.

The optional step 66 of imaging the cut bone to check the intervertebral disc prosthesis fit can be used to confirm proper bone cutting has been performed prior to intervertebral disc prosthesis implantation. In the event that the imaging step 66 shows that optimal fit has not been achieved, further cutting can be performed by returning to step 58. Alternatively, in the event that the imaging step 66 shows that the optimal fit has not been achieved, a different intervertebral disc prosthesis can be selected with a better fit.

Imaging Systems

The methods of creation of the 3D model of the vertebrae and location of and tracking of the vertebrae described herein are examples of the systems that may be used. The surgical methods are not meant to be limited to any particular imaging methods or systems and bone tracking methods. The imaging system generates a 3D model of at least the vertebrae above and below the natural disc to be replaced and can also generate a 3D model of additional anatomic structures. This 3D model can be based on a number of different imaging modalities including imaging with X-ray, CT scan, MRI, photograph or a combination of these methods. The images can be taken preoperatively, intraoperatively or a combination thereof.

In one example, a preliminary 3D model of the anatomical area for surgery is created from preoperative CT scan data. Software or the surgeon can use the preliminary 3D model to make a preliminary determination of the intervertebral disc prosthesis to be selected. This preoperative planning can be used to reduce actual surgery time by having an increased chance of selecting the correct disc from the onset. Once the patient is in surgery, markers are attached to the vertebrae above and below the natural disc to be replaced to allow precise identification of the position and orientation of both of the vertebrae throughout surgery. The 3D model is updated with intraoperative fluoroscopic image data or other image data of the vertebrae having the markers to allow real time 3D tracking of the precise position of the vertebrae above and below the disc to be replaced throughout surgery.

A number of different types of 3D imaging markers are known to be used in surgical robotics. Radiopaque surgical markers can include those that are affixed to bone by screws, pins, adhesives or the like. The radiopaque surgical markers can include a single three dimensional marker for each vertebra or multiple (preferably three) smaller point type markers. One example of a three dimensional marker for use in determining the position of a bone includes a pin for affixing the marker to the bone and a set of three small radiopaque balls arranged in a triangular configuration like a three headed pin. Markers with two, three, four, or more ball arrays can also be used. One alternative marker system uses infrared reflective fiducials. Preferably, the radiopaque markers are small enough to not obstruct the surgical procedure or the surgeon's view of the surgical site, yet large enough to be trackable by the imaging system and be easily located for removal after completion of the procedure. Where small markers are used, they may be inserted robotically and/or removed robotically following the procedure to reduce surgery time and incision size. It is also possible to perform the surgical method without any surgical markers, but by registering and tracking anatomical features or mapping of bone surfaces. In one alternative example, the Caspar pins used for distraction of the vertebrae can themselves be markers or markers can be affixed to the Caspar pins.

The radiopaque markers, mapped bone surfaces or registration of anatomical features allows the imaging system to identify positions of first and second vertebrae and generate and store position data for the positions of the first and second vertebrae in a computing system which transmits this information to a robot control system. The positions of the first and second vertebrae determined from the 3D model of first and second vertebrae at a location of a disc to be replaced from pre-operative and/or intraoperative imaging techniques are used in the subsequent steps of robotic controlled bone preparation. Preferably, the imaging system will continuously verify the positions of the first and second vertebrae throughout the step of robotically guiding the cutting device as the bones may move during surgery.

The imaging system used can be any of the existing image guided surgery systems.

Selecting Discs

The selection of a disc appropriate for the patient can be performed either in the traditional manual manner by inserting one or more trial discs manually, in a robot assisted manner by insertion of one or more trial discs with a robot, or in a virtual manner by inserting virtual trial discs in the 3D model. The traditional manual manner involves beginning by inserting a trial and reviewing the fit both manually and by X-ray and then switching trials until the desired fit is confirmed. Usually the manual fitting process begins with a small size trial implant and sequentially moving to larger sized trial implants until an appropriate fit is determined both visually, via tactile feedback and via X-ray. Implant trials with various lordosis angles may also be tested if available.

The robotic assisted disc selection process uses a robot arm to save time in inserting multiple trial discs of different sizes (height, footprint and/or lordosis) to the same location between the vertebrae and adjusting the size and fit until an optimal fit is achieved. This robotic assisted disc selection process is described further in U.S. Provisional Patent Application No. 62/735,701 titled "Robot Assisted Intervertebral Disc Prosthesis Selection and Implantation System and Method" filed on Sep. 24, 2018 and in co-pending Utility patent application Ser. No. 16/578,949 with the same title filed on even date herewith both of which are incorporated herein by reference. Where the disc is selected manually or by robotic assistance, the finally determined desired disc position is recorded by the 3D image system for use in the steps of planning the bone cuts.

In order to select a disc which is of an appropriate size and function for the patient in a virtual manner with the 3D imaging system, the 3D image is compared to a set of virtual disc data which is provided to appropriate 3D imaging software. The virtual discs correspond to the size and shape and possibly also the function of the actual available intervertebral disc prostheses that could be used for the patient.

Figure 4:
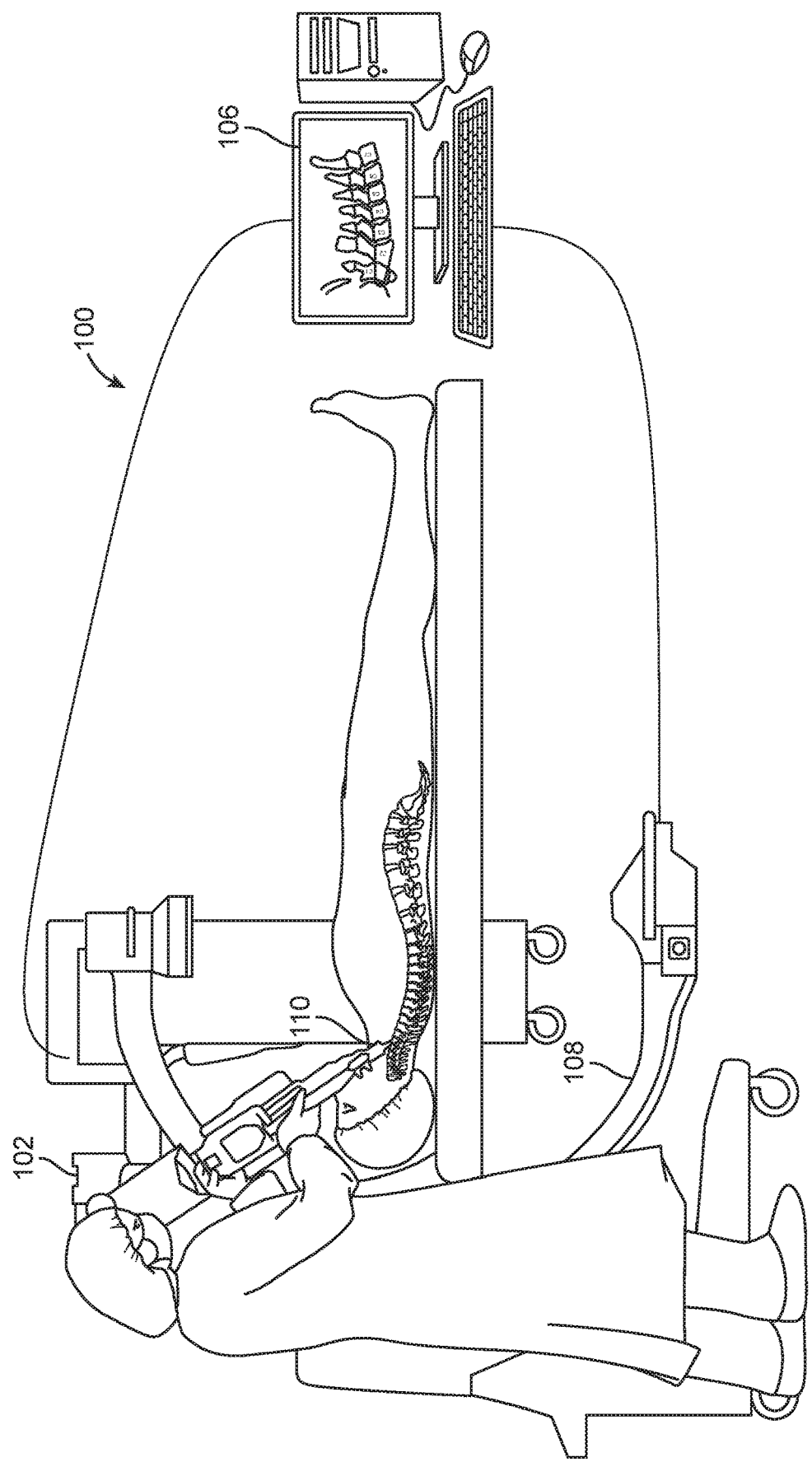
FIG. 4 is a schematic view of a surgical system for robotically preparing a vertebral disc space for implantation of an intervertebral disc prosthesis.

FIG. 4 is a schematic view of a surgical system 100 for robotically preparing a vertebral disc space for implantation of an intervertebral disc prosthesis. The surgical system 100 includes a robot 102 for cutting or guiding a cutting device, an imaging device 104, such as a fluoroscope on a C-arm and a computer system 106 or processing system. The imaging device 104 is preferably mounted on a movable support system such as a C-arm 108 which allows the imaging device position to be controlled by the computer system 106. Preoperative or intraoperative images taken with the imaging device 104 or other imaging system allow the computer system 106 to generate and store position data for the positions of the first and second vertebrae.

The computer system 106 or the surgeon with assistance from the computer system then select an intervertebral disc prosthesis to be implanted by use of the 3D model in combination with physical or virtual trial implants. The desired location for the selected intervertebral disc prosthesis with respect to the positions of the first and second vertebrae position data for the intervertebral disc prosthesis location is stored in the computer system 106. The computer system 106 or the surgeon with assistance from the computer system then determines bone to be cut based on the position data for the first and second vertebrae and the position data for the selected intervertebral disc prosthesis. Finally, the computer system 106 controls the robot 102 to robotically guide a cutting device 110 connected to or guided by the robot to cut the bone in a preselected pattern to fit the selected intervertebral disc prosthesis.

Figure 5:
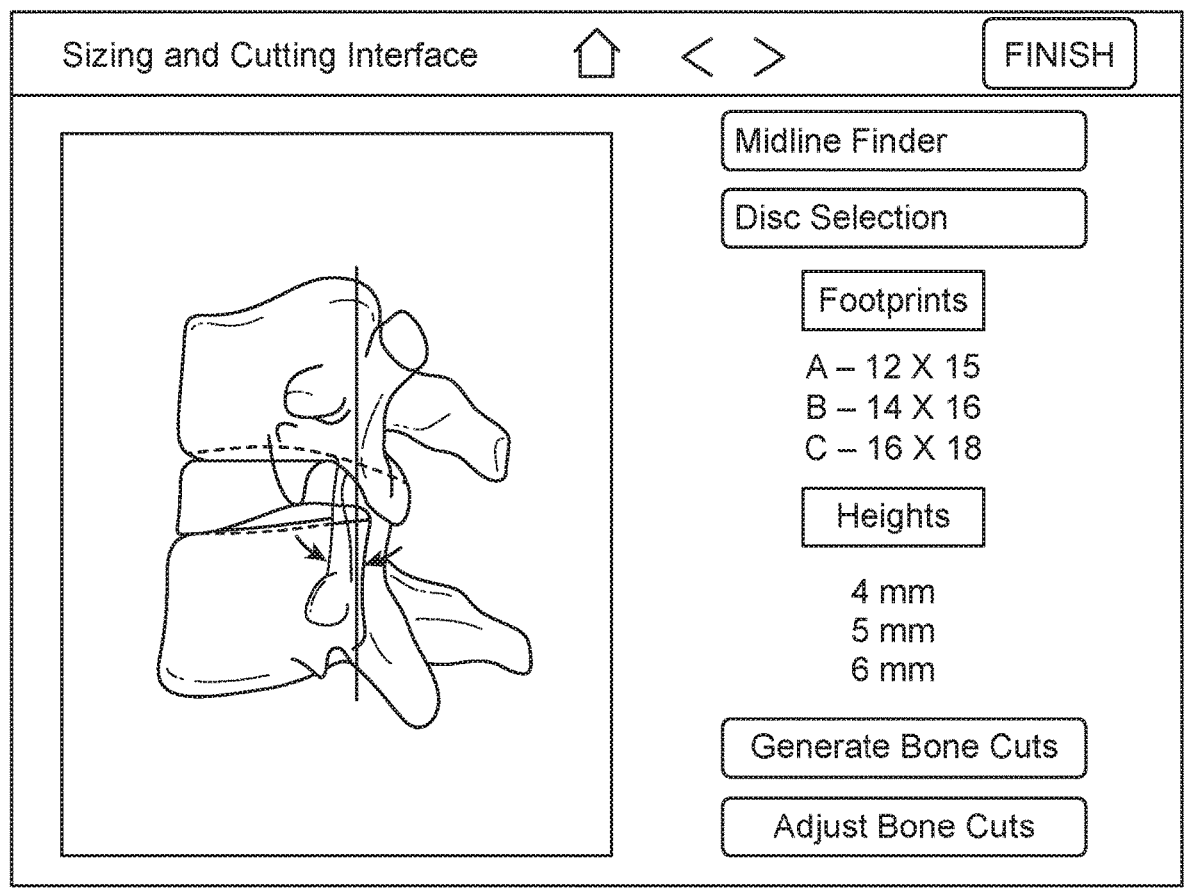
FIG. 5 is a view of a display interface showing a 3D model of two adjacent vertebrae and a position for an intervertebral disc prosthesis.

FIG. 5 illustrates one example of a computer interface which can be displayed on a computer monitor, laptop computer, tablet or other device and used in selecting an intervertebral disc prosthesis and planning bone cutting for optimal placement of the selected intervertebral disc prosthesis. The interface of FIG. 5 includes both virtual disc selection features and planning of bone cutting, however, the bone cut planning features can be used independent of the disc selection features.

The interface includes options for finding a midline, selection of a disc, generation of bone cuts and adjustment of bone cuts. Other options which may be available include determination of center of rotation location. The three dimensional image of the vertebrae on the left side of the interface can be rotated by the user to view different angles. The image is also used to test the fit of a selected intervertebral disc prosthesis. By selection of an intervertebral disc prosthesis footprint size and height on the interface, the virtual disc data generates an image of a virtual disc prosthesis which is overlaid on the 3D image of the vertebrae to test the fit. The fit can be viewed from different angles on the virtual image or model. This viewing from multiple angles is superior to viewing fluoroscopically during surgery as it both reduces radiation exposure and increases the number of viewing angles available (i.e. imaging through the patient's shoulder is difficult and imaging from beneath the surgical table is not possible).

Although FIG. 5 shows a single three dimensional image of the vertebrae which is rotatable, the computer interface alternatively includes 4 orthogonal views as well as one or more trajectory views of the vertebrae. Other computer interfaces can include separate interfaces for the steps of disc selection, determining bone cutting, and robotic cutting. The surgeon can use the computer interface to make and/or adjust a cutting plan for robotic cutting of the vertebrae. Although the robotic method has been described as first selecting a disc or implant followed by robot assisted cutting of the bone to match the disc or implant, it is also contemplated that the method can reverse these steps. In an alternative robotic method, the bone is first cut in a pattern or configuration selected to match a series of implants and the implanted is selected after cutting to match the precise size and/or shape of the prepared disc space.

Optional Step of Distraction Prior to Disc Selection

Preferably, the disc space between the two vertebrae is distracted and the natural disc is removed by discectomy prior to the process of selecting the disc. In one example, distraction is performed by use of a Caspar distractor and distractor pins which allow parallel distraction of the vertebrae. Distraction prior to disc selection provides a more reliable fit of the implant.

In one embodiment, the distraction step can be performed robotically. A robotic distraction process is described further in U.S. Provisional Patent Application No. 62/735,710 filed Sep. 24, 2018 and titled "Robotic Systems and Methods for Distraction for Intervertebral Disc Prosthesis Placement" and co-pending U.S. Utility patent application Ser. No. 17/485,066, and U.S. Pat. No. 11,160,672, all of which are incorporated herein by reference. The robotic distractor can be pivotable to control distances between vertebrae in multiple planes and can avoid over distraction injury while reducing forces on the implant cause by under distraction.

Determining Bone to be Cut for Disc Prostheses with Fins

When the selected intervertebral disc prosthesis selected in step 54 is a disc with one or more fin, such as the disc 10, the step of robotically guiding the cutting device 62 robotically cuts a channel in the bone in a predetermined plane and of a predetermined depth to receive a fin of the intervertebral disc prosthesis of the correct size, shape and depth. When the robotic guiding device of step 64 is used, a guiding device on the end of the robot effector is used to guide the cutting or shaping. The guiding device may include a tube through which the cutting tool is movably received or grasper which grasps the cutting tool in a fixed manner with respect to the robot end effector. Once the cutting tool is guided by the guiding device, the robot guides the tip of the cutting device or cutter in an exact plane of a desired cut and allows cutting only in the plane of the desired cut. The guiding device also stops the cutter from cutting beyond a desired depth.

In the case of a central midline fin 18, such as shown in the disc 10 of FIG. 1, the robotic cutting or guiding is located at the midline of the vertebral bodies adjacent a disc space. The location of the midline of the vertebral bodies can be determined from imaging data and the 3D model. The system then includes robotically cutting one or more channel on the midline of the vertebral bodies based on the imaging data.

Traditionally, manual cutting of a channel for a fin is performed with a cutting tool in the form of a serrated or unserrated manual slot cutter with which a surgeon uses a mallet to hammer the cutter into the bone. According to a first embodiment, the robot provides a guide which receives the slot cutter in an orientation such that the slot cutter will be guided to cut the slot in a predetermined plane and to a predetermined depth. The impact on the slot cutter for cutting can be provided either manually with a mallet or robotically.

In another embodiment, the manual slot cutter is replaced with a bone saw or rotary burr which cuts the bone slot robotically. In one version, for an anterior cervical disc procedure, the saw or burr is placed at the posterior end of the slot to be cut and is moved outward toward the anterior edge of the vertebrae in order to cut the bone while eliminating any chance of cutting excessively deep. With this outward cutting technique, the anterior edge of the vertebrae can be braced against a portion of the robot and motion of the vertebrae during cutting can be minimized.

Determining Bone to be Cut for Intervertebral Disc Prostheses with Special Shapes When the selected intervertebral disc prosthesis selected in step 54 is a disc with one or more special features or shapes, such as the central dome 38 shown in the disc 30 of FIG. 2, the step of robotically guiding the cutting device shapes the bone to substantially match the shape of the outer vertebral contacting surface of the intervertebral disc prosthesis. In the case of a prosthesis with a dome, the robotic cutter or guided cutter cuts a concave shaped recess (such as a spherical or cylindrical dome shaped recess) in one or both of the first and second vertebrae of a predetermined depth and radius for receiving the dome of the intervertebral disc prosthesis. The system can locate the recess at a location determined to cause the disc to be placed with a center of rotation of the disc prosthesis as close as possible to the natural center of rotation of the natural healthy disc. Once the dome shaped recess has been cut in the vertebra, the disc prosthesis is placed either manually or robotically and the dome of the disc prosthesis fits (on the upper and/or lower prosthesis plate) into the recess in the desired position.

The shaping of the bone to receive special shapes of the upper and lower plates of the disc prosthesis also can be used to appropriately align the upper and lower plates in the patient. Misalignment in which one plate is misaligned with respect to the other plate can be a source of vertebral instability and can be eliminated by the robotic bone preparation system.

Determining Bone to be Cut for Flat Endplates

When the surfaces of the vertebrae are not flat and a flat plate of an intervertebral disc prosthesis is to be placed against the vertebrae a lack of good bone to implant contact can allow the implant to migrate. To minimize such migration, a surgeon can shape the vertebra surface, such as with a high speed surgical power tool with a cutting burr, to match the flat shape of the implant endplates. The robotic bone preparation system can use preplanned cutting in a predetermined cutting pattern to robotically cut bone in a manner which minimizes the amount of bone removed while achieving a good bone to implant fit. Minimizing the bone removed can maximized strength of vertebra reduce the chances of implant subsidence. The surgeon can select among a number of different settings to plan for an amount of bone to be removed depending on surgeon preference for bone removal between minimal bone removal to greater bone removal and better implant fit.

Removal of the Uncinate Process

Figure 6:
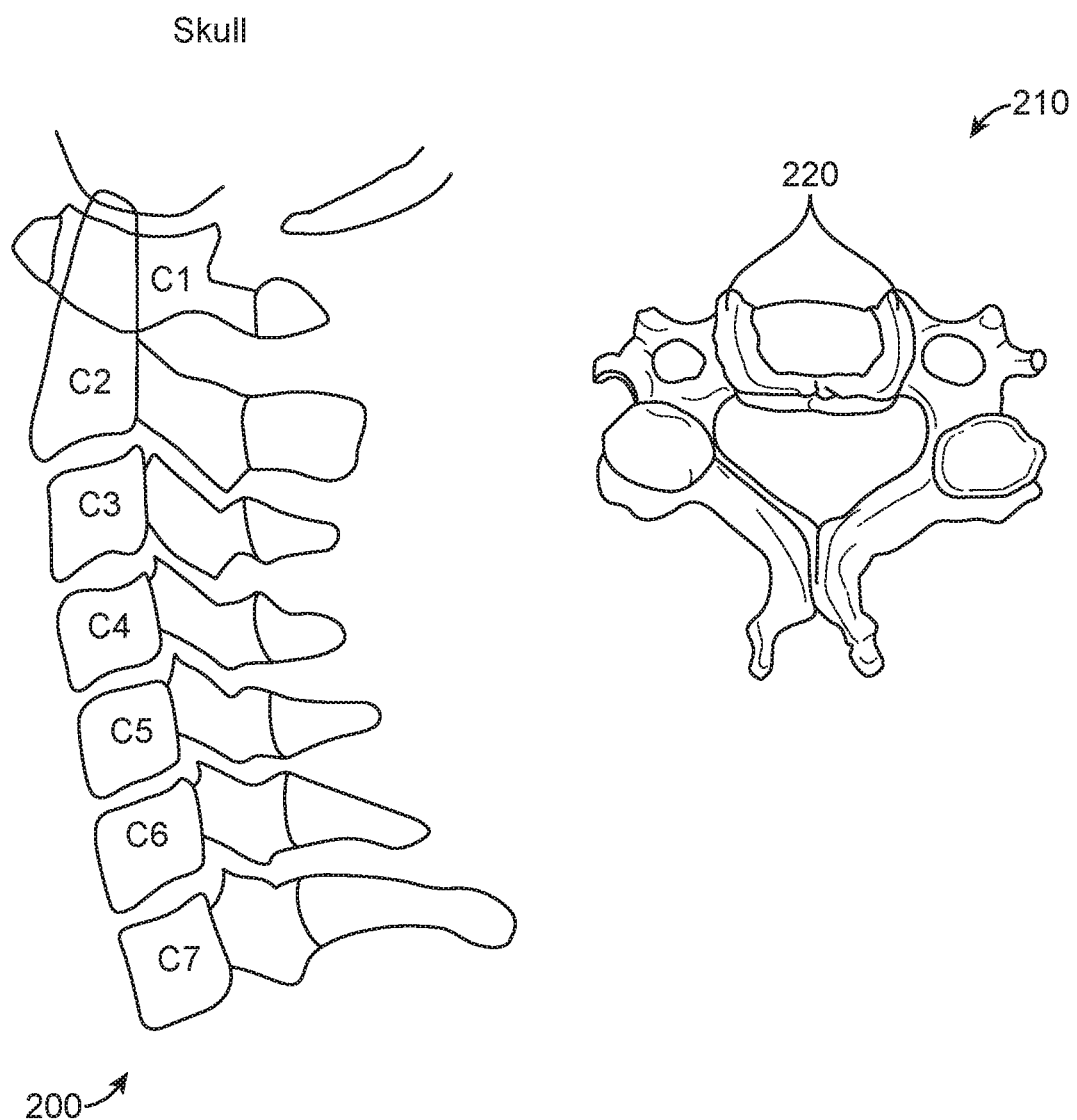
FIG. 6 is a schematic illustration of a cervical spine.

In addition to shaping the upper or lower surfaces of the vertebrae adjacent to the disc space to accommodate the intervertebral disc prosthesis, there may be other boney structures around the disc space which need to be removed to achieve optimum disc prosthesis fit and function. The cervical spine 200 and a single vertebra 210 of the cervical spine are shown in FIG. 6. The robotic systems and methods of the present invention can be used an any one or multiple of the disc levels C1-C7 shown in FIG. 6 or in one or more levels of the lumbar or thoracic spine. The uncinate process 220 of the cervical spine is a hook-shaped process found bilaterally on the superolateral margin of the cervical vertebral bodies. The uncinate processes are more anteriorly positioned in the upper cervical spine and more posteriorly located in the lower cervical spine and function to limit lateral flexion and maintain the position of the intervertebral discs during axial rotation. The uncinate process can limit the size (width) of implant that can be used and in many cases are removed partially or fully before implant placement. A preoperative planning process can select a disc prosthesis width which is appropriate for the disc space after removal of the uncinate processes. The robotic bone preparation system can use preplanned cutting in a predetermined cutting pattern to robotically cut the uncinate process to achieve a good bone to implant fit with a disc footprint size which maximizes bone coverage and reduces implant subsidence. The surgeon can use the computer interface to identify the amount and location of the uncinate process to be removed.

Determining Bone to be Cut when Bone Osteophytes or Malformations are Present

When bone osteophytes or malformations are present on the vertebrae adjacent the disc space where the intervertebral disc prosthesis is to be implanted, these bone features can adversely affect the placement of the implant. The steps of determining bone to be cut and robotically guiding the cutting device can involve planning for and using the cutting device to remove osteophytes or other malformation identified in the 3D model which would affect implant placement or surgeon access to the disc space for implant placement. The osteophytes or malformations can also affect the eventual motion of the disc prosthesis by restricting motion and may be removed to allow full range of motion.

The surgeon can use the computer interface to make and/or adjust a cutting plan for robotic cutting of the vertebrae including where bone osteophytes are presesnt. For example, where the surgeon sees boney malformations or osteophytes which may prevent a full range of motion after surgery, the surgeon can identify area(s) to be cut on the 3D image on the interface so that these areas can be cut during the robotic cutting step.

Determining Bone to be Cut to Optimize Location of Disc Center of Rotation

By reshaping the bone at the surgical site to create the optimally positioned cavity to receive the implant the robotic bone preparation system can help to place the intervertebral prosthetic disc at the optimal location to match the prosthetic disc center of rotation to the center of rotation of a natural healthy disc.

Posterior and Lateral Lumbar Intervertebral Disc Prostheses

For posterior or lateral lumbar intervertebral disc prosthesis procedures, the steps of determining bone to be cut can include determining the trajectory for insertion of the bone cutting tool. With posterior and lateral lumbar disc procedures accessing the disc space past sensitive structures at the posterior of the spine is delicate and can be problematic. Preplanning the access route as well as the bone to be removed can be beneficial in both time and safety. The step of robotically guiding the cutting device from the posterior or lateral side of the spine can involve planning for the trajectory of access of the cutting device as well as robotically using the cutting device to remove bone identified in the 3D model.

Cutting Access While Avoiding Sensitive Structures

Accessing the disc space from the anterior of the spine can also involve avoiding sensitive structures including the esophagus, trachea, nerves and blood vessels. In one example, removal of the uncinate process as described above requires cutting in close proximity to the vertebral artery. The 3D model can be updated to include the location of the nearby blood vessels and/or spinal nerves and the access route for the cutting tool as well as the bone to be removed can be determined based on the additional information of the surrounding sensitive structures. Updating of the 3D model to locate blood vessels, nerves and other important anatomic structures can be achieved by nerve monitoring, by identification of the structures during surgery by the surgeon with a position sensing device or digitizer or by soft tissue visualization techniques. These structures, once located, can be avoided in the robotic cutting process. Robot assisted access to the disc space can be particularly advantageous in multi-level surgical procedures where the intricacy of the procedure increases.

Interbody Fusion Procedures

Although the robotic surgical systems and methods have been described for use in preparation of vertebrae to accommodate an intervertebral disc prosthesis, the systems and methods described herein may also be used for improved precision and optimal performance of other spinal implants including interbody fusion devices, interspinous spacers, vertebral body replacements. The robotic surgical systems and methods can be used to assist the surgeon in preventing potential improper positions of these other implants including assisting in placing the implants on the midline of the adjacent vertebrae, in the proper position in the anterior posterior direction, and aligned with other implanted devices in the same or another level of the spine.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. A surgical method for preparing a vertebral disc space for implantation of an intervertebral disc prosthesis, the method comprising:
identifying positions of first and second vertebrae and generating and storing position data for the positions of the first and second vertebrae in a computing system;
selecting the intervertebral disc prosthesis to be implanted between the first and second vertebrae;
determining a desired location for the selected intervertebral disc prosthesis with respect to the positions of the first and second vertebrae and a center of rotation for the intervertebral disc prosthesis and storing position data for the intervertebral disc prosthesis location and the center of rotation;
determining a preselected pattern of bone to be cut based on the position data for the first and second vertebrae and the position data for the center of rotation for the selected intervertebral disc prosthesis; and
robotically guiding a cutting device to cut the bone in the preselected pattern to fit the selected intervertebral disc prosthesis.

2. A surgical method of claim 1, wherein the step of robotically guiding the cutting device comprises attaching a cutting tool to a robot end effector and robotically controlling the cutting tool to cut the bone in a desired pattern without a surgeon's hand on the tool.

3. A surgical method of claim 1, wherein the step of robotically guiding the cutting device comprises robotically guiding a guiding device to a desired position for cutting the bone and manually cutting the bone by inserting a cutting tool in the guiding device.

4. A surgical method of claim 1, wherein the step of robotically guiding the cutting device comprises robotically guiding a manual cutting device to prevent cutting at a no cut location.

5. A surgical method of claim 1, wherein the step of robotically guiding the cutting device comprises cutting a channel in the bone in a predetermined plane and of a predetermined depth to receive a fin of the intervertebral disc prosthesis by guiding the cutting device to move only in the predetermined plane until the predetermined depth is reached.

6. A surgical method of claim 1, wherein the step of robotically guiding the cutting device comprises placing a tip of a cutter in a plane of a desired cut and limits cutting to the plane of the desired cut.

7. A surgical method of claim 1, wherein the step of robotically guiding the cutting device comprises cutting a dome shaped recess in one or more of the first and second vertebrae of a predetermined depth and radius for receiving a dome of the intervertebral disc prosthesis.

8. A surgical method of claim 1, wherein the step of identifying the positions of the first and second vertebrae comprises:
developing a three dimensional model of the first and second vertebrae at a location of a disc to be replaced from pre-operative imaging techniques; and
continuously verifying the positions of the first and second vertebrae throughout the step of robotically guiding the cutting device.

9. A surgical method of claim 8, further comprising placing a plurality of radiopaque markers in the first and second vertebrae for verifying the positions of the first and second vertebrae.

10. A surgical method of claim 1, wherein the step of robotically guiding the cutting device comprises using the cutting device to remove osteophytes.

11. A surgical method of claim 1, further comprising robotically implanting the selected intervertebral disc prosthesis between the first and second vertebrae, wherein the first and second vertebrae have been cut to fit the selected intervertebral disc prosthesis.

12. A surgical method of claim 11, wherein the selected intervertebral disc prosthesis comprises:
a first plate having an outer surface locatable against the first vertebra and an inner bearing surface; and
a second plate having an outer surface locatable against the second vertebra and an inner bearing surface,
wherein the inner bearing surfaces of the first and second plates allow the plates to articulate and translate with respect to one another.

13. A surgical method of claim 1, wherein the vertebral disc space for implantation of the intervertebral disc prosthesis is a cervical vertebral space.

14. A surgical method of claim 1, wherein the vertebral disc space for implantation of the intervertebral disc prosthesis is a lumbar vertebral space and the step of robotically guiding a cutting device to cut bone accesses the vertebral space with the cutting device from a posterior or lateral side of the vertebral space.

15. A surgical method of claim 1, wherein the first and second vertebra are adjacent to one another.

* * * * *